(12) United States Patent
Heinz (10) Patent No.: US 7,578,823 B2
(45) Date of Patent: Aug. 25, 2009

(54) DELIVERY TOOL AND METHOD FOR DELIVERING BONE GROWTH MATERIAL

(75) Inventor: Eric Steven Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 306 days.

(21) Appl. No.: 11/118,817

(22) Filed: Apr. 29, 2005

(65) Prior Publication Data

US 2006/0247652 A1    Nov. 2, 2006

(51) Int. Cl.
    *A61B 17/58*    (2006.01)
(52) U.S. Cl. ....................................... 606/92
(58) Field of Classification Search ............. 606/92–94, 606/106–108; 604/15, 36–38, 64, 187, 218, 604/224, 311; 227/175.1
    See application file for complete search history.

(56) References Cited

U.S. PATENT DOCUMENTS

| | | | | |
|---|---|---|---|---|
| 1,019,465 | A | * | 3/1912 | Harrison ...................... 604/58 |
| 2,647,512 | A | * | 8/1953 | Johnson ....................... 604/64 |
| 3,744,493 | A | * | 7/1973 | Booher et al. .................. 604/62 |
| 4,871,094 | A | * | 10/1989 | Gall et al. .................... 222/386 |
| 4,995,867 | A | * | 2/1991 | Zollinger .................... 604/514 |
| 5,830,152 | A | * | 11/1998 | Tao ............................ 600/562 |
| 6,019,765 | A | | 2/2000 | Thornhill et al. |
| 6,383,190 | B1 | | 5/2002 | Preissman |
| 6,547,467 | B2 | * | 4/2003 | Quintero ..................... 401/132 |
| 6,793,660 | B2 | | 9/2004 | Kerr et al. |
| 2002/0049448 | A1 | | 4/2002 | Sand et al. |
| 2003/0069545 | A1 | | 4/2003 | Arm |
| 2004/0215201 | A1 | | 10/2004 | Lieberman |
| 2004/0225295 | A1 | | 11/2004 | Zubok et al. |
| 2004/0260303 | A1 | * | 12/2004 | Carrison ...................... 606/92 |
| 2005/0165408 | A1 | | 7/2005 | Puno et al. |

* cited by examiner

*Primary Examiner*—Thomas C Barrett
*Assistant Examiner*—Nicholas Woodall (57) ABSTRACT

A delivery tool and method for placing bone growth material at an operative location a patient is provided. The delivery tool includes a housing having a chamber for receiving the bone growth material and a delivery mechanism operably coupled to the housing to displace the bone growth material through the chamber to a distal opening of the chamber for delivery to the operative site.

17 Claims, 7 Drawing Sheets

DELIVERY TOOL AND METHOD FOR DELIVERING BONE GROWTH MATERIAL

BACKGROUND

It may be desirable to fill a space in a bone or implant with material to facilitate bone growth for fusion or other therapeutic treatment. The material may be permanent or temporary, and may also include one or more agents to promote healing. Delivery of the material may be impeded by the nature, size and shape of the material particles, viscosity or other properties. Tools and methods which facilitate the application of the necessary forces to deliver such materials at remote locations remote can reduce operating time and result in more effective placement of the material at the operative site.

SUMMARY

The invention provides tools and methods for delivering bone growth material in surgical procedures.

According to one aspect, there is provided a tool for delivery of bone growth material to an operative site. The tool includes a mounting member having a passage extending longitudinally therethrough and a housing mounted to a distal portion of the mounting member. The housing includes a sidewall extending about a longitudinal axis that defines a loading chamber and a dispensing chamber distal of the loading chamber. The housing further includes an access port in the sidewall in communication with the loading chamber. The access port is configured to receive bone growth material for depositing in the loading chamber. A driver is engaged to the mounting member with a distal end portion of the driver received in the loading chamber. The driver is longitudinally movable in the loading chamber to displace bone growth material therein toward a distal end of the dispensing chamber.

According to another aspect, a tool for delivery of bone growth material to an operative site is provided. The tool includes a mounting member with a longitudinal passage and a housing mounted to a distal portion of the mounting member. The housing includes a sidewall extending about a longitudinal axis that defines a loading chamber and a dispensing chamber. A driver is engaged to the mounting member that includes a distal gripping assembly with a tip removably engaged thereto. The tip is selected from a staging tip having a first cross-section at a distal end thereof and a dispensing tip having a second, smaller cross-section at a distal end thereof. The selected tip is longitudinally movable in the loading chamber with the driver to displace bone growth material toward a distal end of the dispensing chamber.

According to another aspect, a method for delivering bone growth material to an operative location in a patient is provided. The method includes placing bone growth material in a loading chamber of a housing; manipulating a driver mounted to the housing to distally advance a staging tip at a distal end of the driver; advancing the staging tip distally through the loading chamber to displace bone growth material from the loading chamber to a staging chamber distally of the loading chamber; removing the staging tip; attaching a dispensing tip to the distal end of the driver; manipulating the driver to distally advance the dispensing tip; and advancing the dispensing tip distally through the staging chamber into a dispensing chamber to dispense bone growth material through a distal opening of the housing.

These and other aspects can be discerned from the following written description and accompanying figures.

DESCRIPTION OF THE ILLUSTRATED EMBODIMENTS

For the purpose of promoting an understanding of the principles of the invention, reference will now be made to the illustrated embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

A delivery tool and method for placing bone growth material in a patient at an operative site is provided. The delivery tool includes a housing having a chamber for receiving the bone growth material and a delivery mechanism operably coupled to the housing to displace the bone growth material through the chamber to a distal opening of the chamber. The chamber can be elongated and sized to permit access to locations in the patient that are difficult to access for manual placement of the bone growth material.

Figure 1:
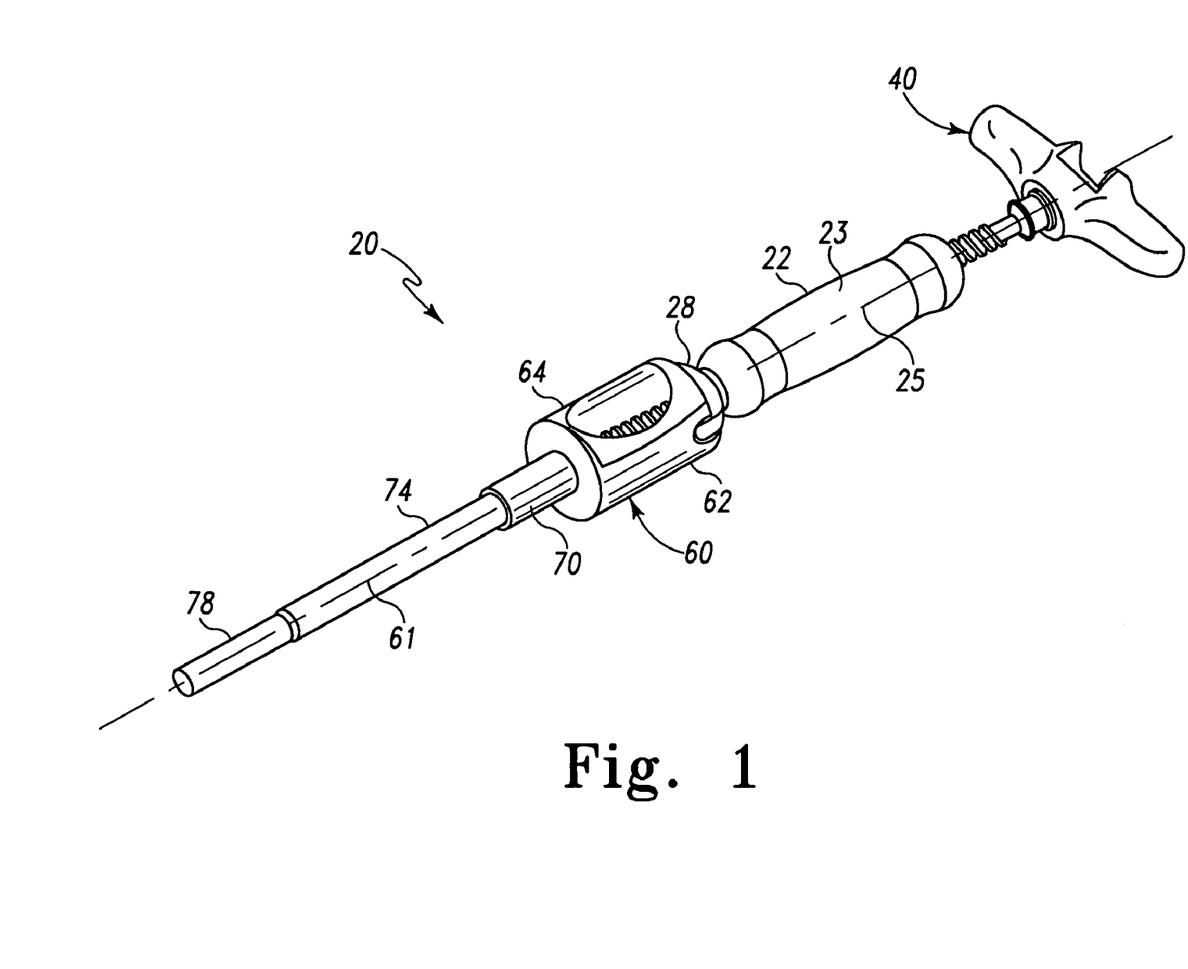
FIG. 1 is a perspective view of a bone growth material delivery tool.
Figure 2:
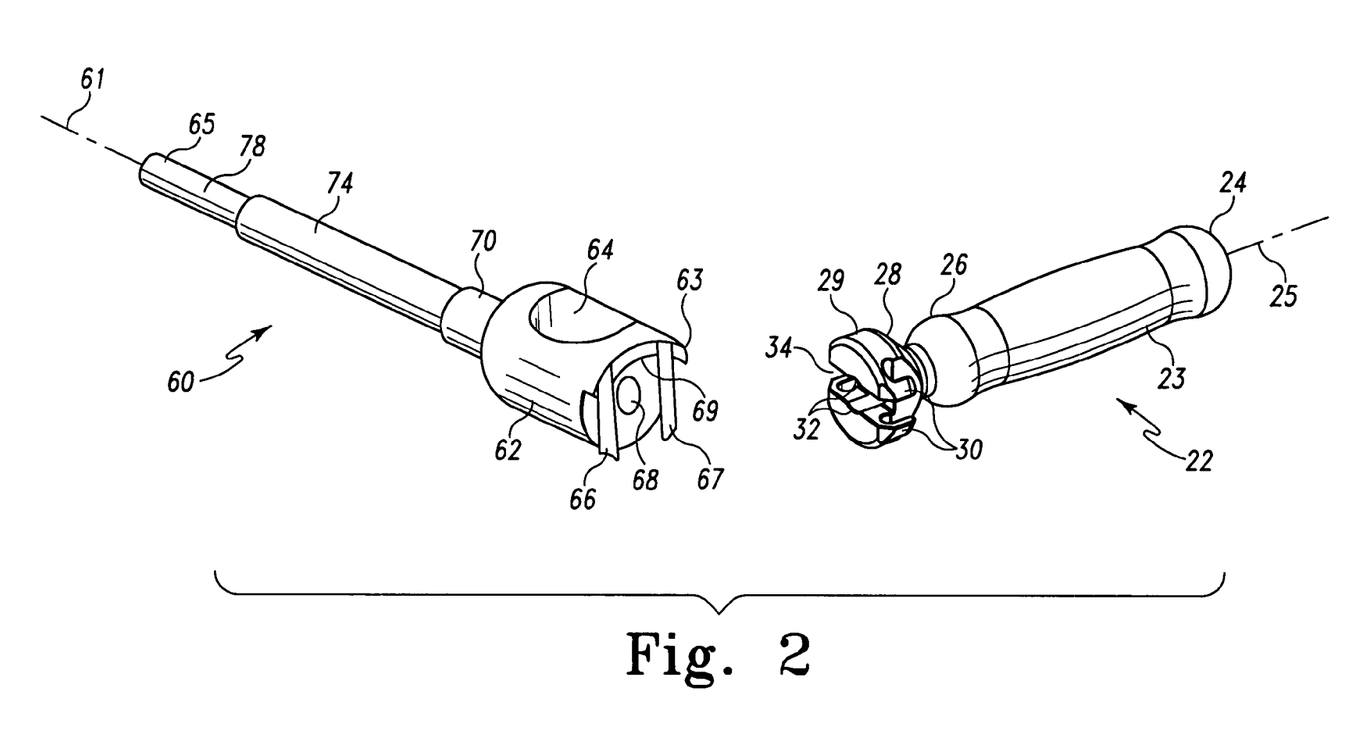
FIG. 2 is an exploded view of a housing and mounting member of the tool of FIG. 1.
Figure 3:
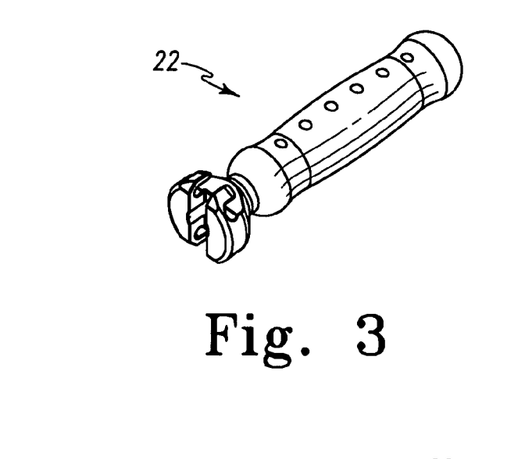
FIG. 3 is a perspective view of the housing.
Figure 4:
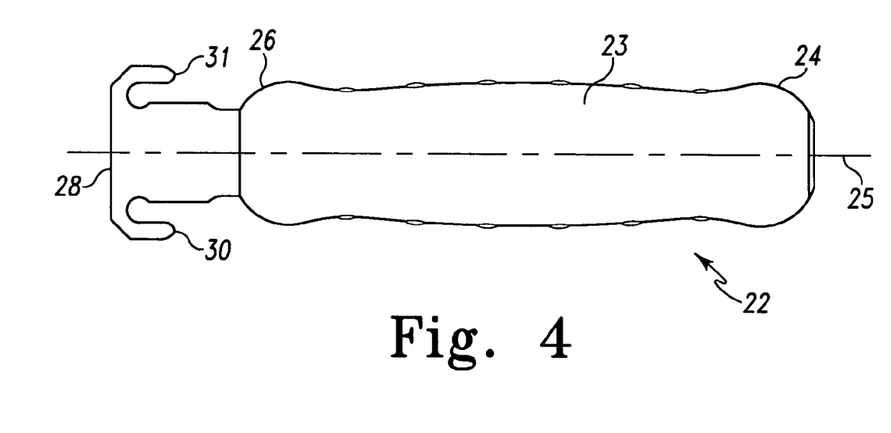
FIG. 4 is an elevation view of the housing of FIG. 3.
Figure 5:
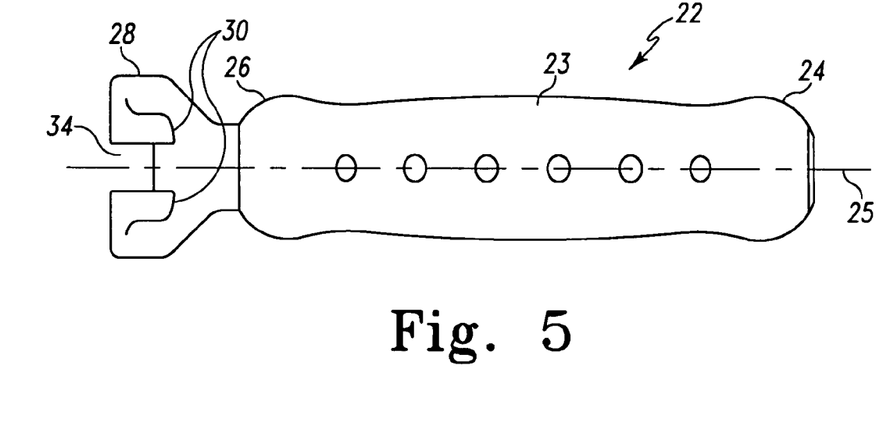
FIG. 5 is an elevation view of the housing of FIG. 4 rotated 90 degrees about its longitudinal axis.
Figure 6:
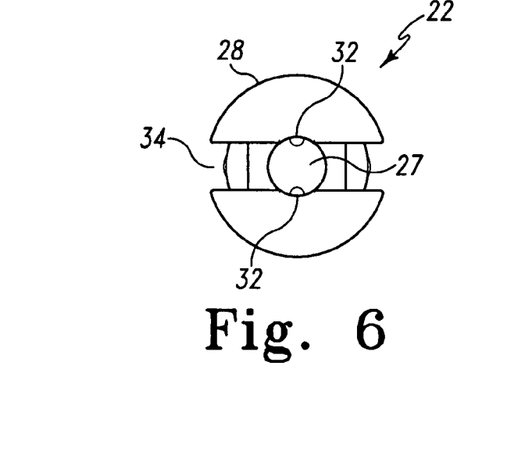
FIG. 6 is a left end elevation view of the housing of FIG. 5.
Figure 7:
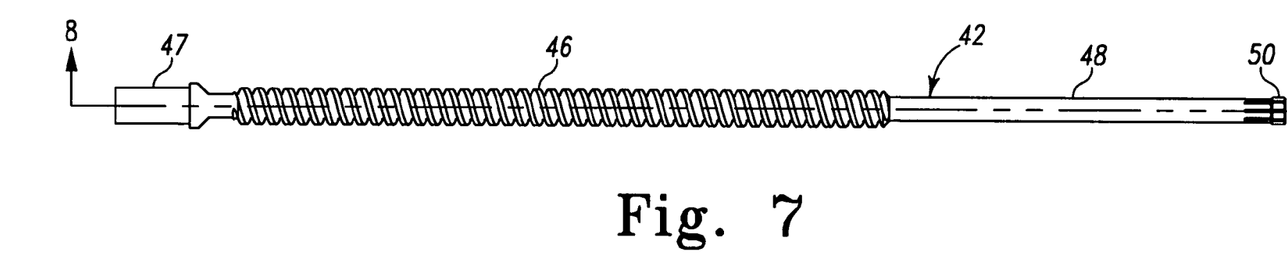
FIG. 7 is an elevation view of a shaft of a driver of the tool of FIG. 1.
Figure 8:
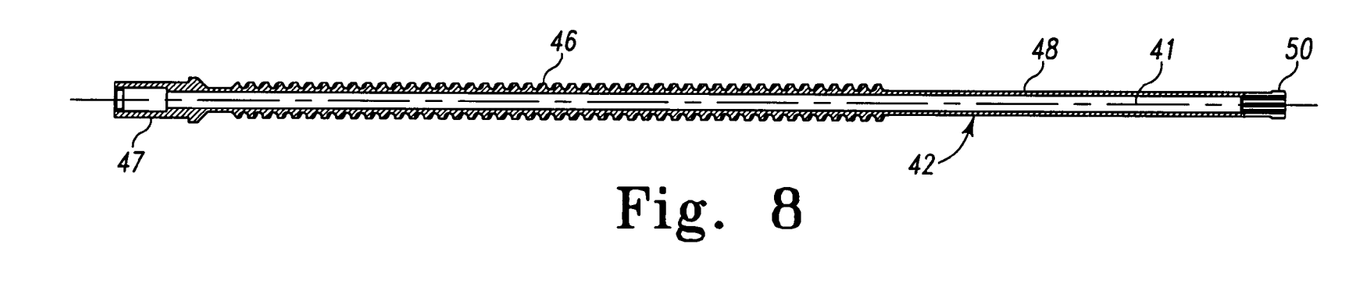
FIG. 8 is a section view along line 8-8 of FIG. 7.
Figure 9:
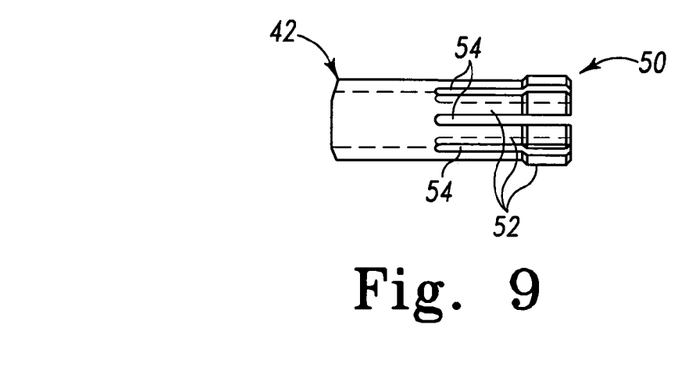
FIG. 9 is an enlarged view of a distal portion of the shaft of FIG. 7.

In FIG. 1 there is shown a delivery tool 20 including a mounting member 22, a driver 40, and a housing 60. Housing 60 is removably mounted to a distal mounting portion of mounting member 22. Driver 40 is positioned through mounting member 22 and into a chamber defined by housing 60. Driver 40 is remotely operable to displace bone growth material in the chamber of housing 60 distally to one or more distal ports to deliver the bone growth material to the operative site.

Referring further to FIGS. 2-6, mounting member 22 includes a handle portion 23 extending between a proximal end 24 and a distal end 26 along a longitudinal axis 25. A mounting portion 28 extends from distal end 26. Mounting portion 28 includes a first pair of U-shaped fingers 30 and a second pair of U-shaped finger 31 on the opposite side thereof. The paired fingers 30, 31 each form a U-shaped receptacle that receives housing 60 in releasable engagement, as discussed further below. A groove 34 extends trans-axially between and divides the paired fingers 30 and also divides the paired fingers 31. Concave recesses 32 in groove 34 extend axially toward an elongate passage 27 that extends through handle portion 23 along axis 25. Driver 40 is received through passage 27 and threadingly engageable with a mounting member 22 therein.

Housing 60 includes an elongated body extending along longitudinal axis 61 between a proximal end 63 and a distal end 65. A passage 68 extends axially through the proximal end wall of housing 60 and opens into a loading chamber 73. At proximal end 63 there is also provided a pair of arms 66, 67 extending parallel to one another transversely to and offset from opposite sides of longitudinal axis 61. Arm 66 is positionable in the U-shaped receptacles formed by fingers 30 on one side of mounting portion 28 of mounting member 22, and arm 67 is positionable in the U-shaped receptacles formed by fingers 31 on the opposite side of mounting portion 28. An upper flange 69 extending between arms 66 is positionable in contact with outer surface 29 of mounting portion 28 extending between the arms pairs 30, 31. When mounted to mounting member 22, passage 68 is aligned with the passage 27 extending through mounting member 22.

Figure 13:
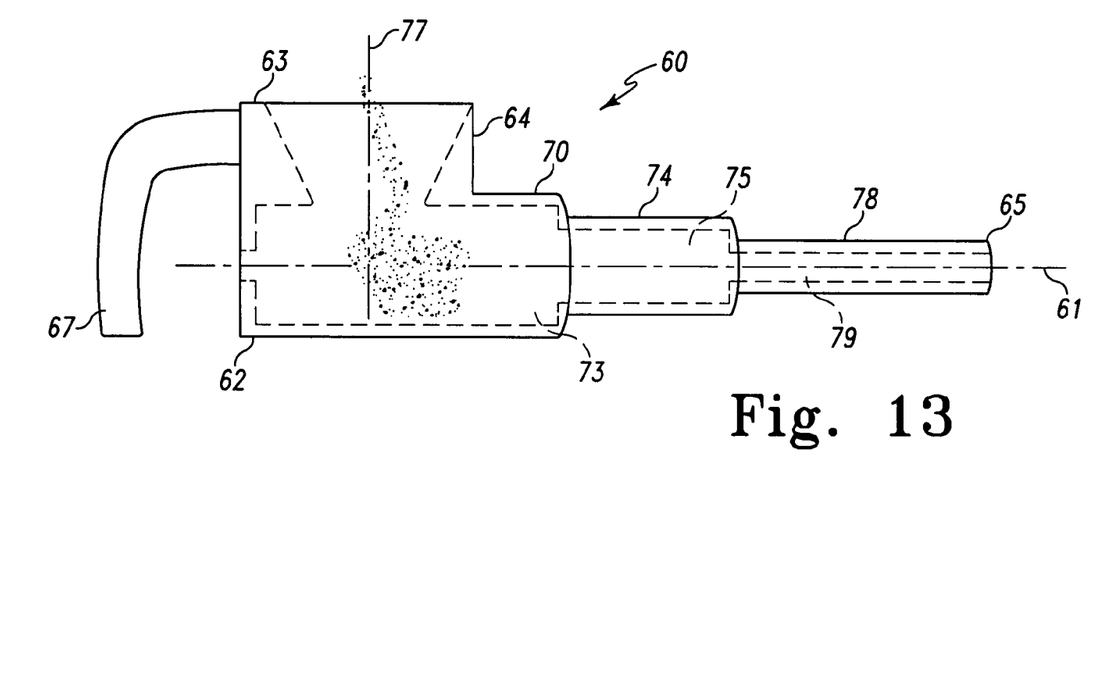
FIG. 13 is an elevation view of the housing of the tool of FIG. 1 with bone growth material being positioned in the loading chamber.

As further shown in FIG. 13, housing 60 includes a loading portion 62 adjacent proximal end 63 that has an outer sidewall extending about longitudinal axis 61. Loading portion 62 includes an access port 64 extending along an axis 77 that is transversely oriented to longitudinal axis 61. Access port 64 provides an opening into a loading chamber 73 defined by the sidewall of loading portion 62. Bone growth material can be deposited through access port 64 and into loading chamber 73.

Loading portion 62 further includes a transition portion 70 extending distally from access portion 64 to a staging portion 74. Staging portion 74 includes a sidewall extending about longitudinal axis 61 that defines a staging chamber 75 in communication with loading chamber 73. Staging portion 74 extends axially to a distal dispensing portion 78. Dispensing portion 78 includes a sidewall extending thereabout that defines a dispensing chamber 79 extending therethrough in communication with staging chamber 75. One or more dispensing outlets, ports or the like may be defined at the distal end 65 of dispensing portion 78. Dispensing portion 78 may further be coupled to an extension that is angled relative to axis 61 or flexible to allow additional options for the positioning of a dispensing outlet.

Driver 40 is further shown in FIGS. 7-10. Driver 40 includes an elongated shaft 42, shown in FIGS. 7-8, extending along a longitudinal axis 41. Shaft 42 includes an intermediate threaded portion 46 and a distal, non-threaded portion 48 extending distally from threaded portion 46. Distal portion 48 includes a gripping mechanism 50 at a distal end thereof. A proximal hub 47 is provided for engagement with a handle member.

Figure 10:
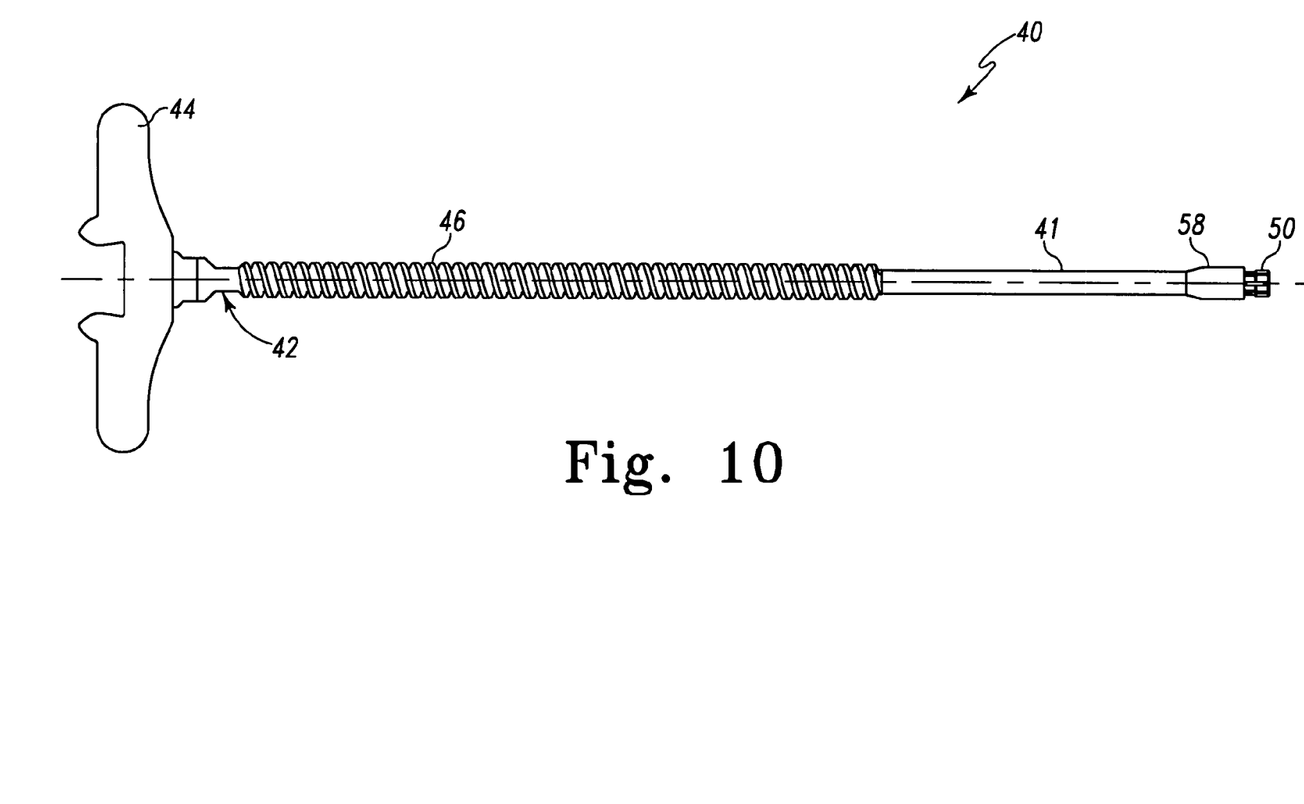
FIG. 10 is an elevation view of the driver of the tool.

As shown in FIG. 10, a handle member 44 can be secured about hub 47 of shaft 42. Gripping mechanism 50 includes a number of gripping members 52 separated from one another by axial slots 54. Gripping members 52 can flex radially outwardly to accommodate insertion of various tip members, as discussed further below. The gripping members 52 resiliently return toward one another to maintain the grip on the tip member positioned therein. An outer sleeve 58 can be positioned along shaft 42 and over a proximal portion of gripping members 52 to limit flexion of gripping members 52 away from one another. Other embodiments contemplate other gripping mechanisms to maintain the tips in engagement with driver 40, including threaded connections, ball-detent mechanisms, bayonet locks, friction fits, adhesives or fusing, clamps, set screws, and other fasteners, for example.

Figure 11:
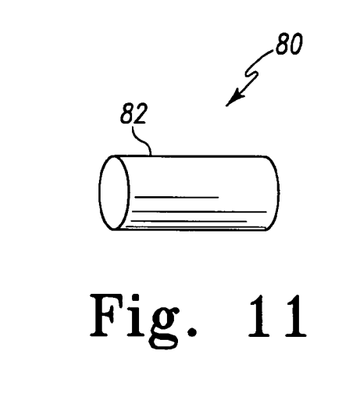
FIG. 11 is a perspective view of a staging tip useable with the tool of FIG. 1.
Figure 12:
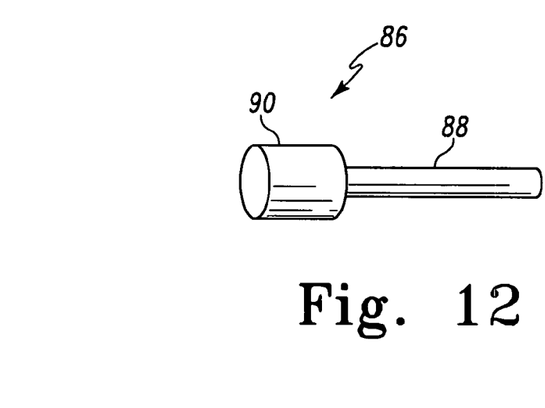
FIG. 12 is a perspective view of a dispensing tip useable with the tool of FIG. 1.

In FIGS. 11 and 12, there are shown various tip members that are engageable with driver 40 and movable therewith to deliver bone growth material from loading chamber 73 to the implantation location in the patient. In FIG. 11 there is shown a staging tip 80. Staging tip 80 includes a cylindrical body of substantially uniform cross-section in the illustrated embodiment. Staging tip 80 can be grasped at one end by gripping mechanism 50 of driver 40.

Figure 14:
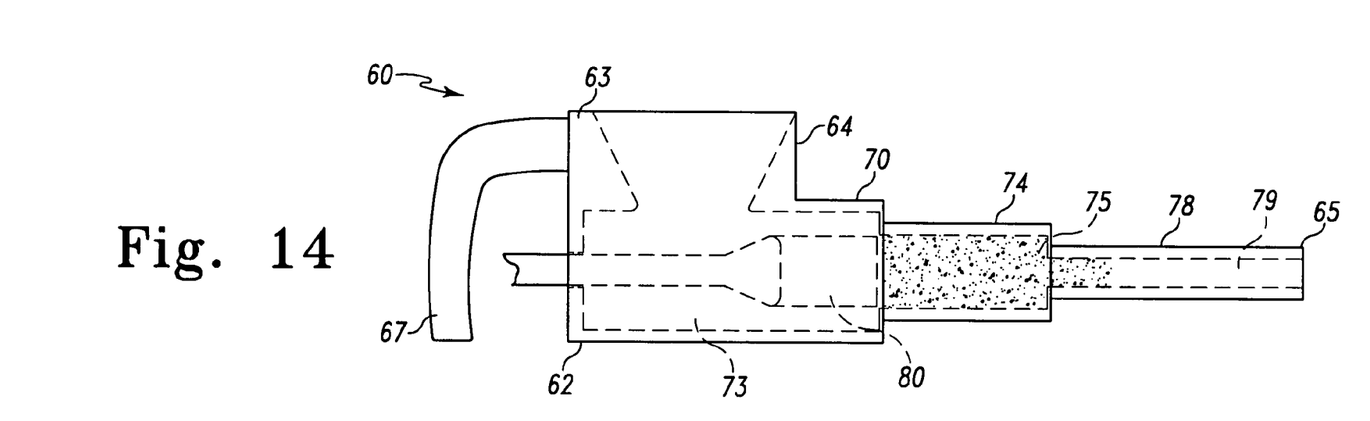
FIG. 14 is an elevation view of the housing and a portion of the driver of the tool of FIG. 1 with bone growth material being packed in the staging chamber of the housing with the staging tip coupled to the driver.

Staging tip 80 extends from gripping mechanism 50 into loading chamber 73 as shown in FIG. 14. Staging tip 80 is movable from loading chamber 73 into staging chamber 75 to displace the bone growth material deposited into loading chamber 73 into staging chamber 75. As staging chamber 75 is filled with bone growth material, placement of additional material into staging chamber 75 with staging tip 80 can also force bone growth material into dispensing chamber 79. Staging tip 80 can be moved longitudinally in the distal and proximal directions by rotating driver 40 in mounting member 22. Staging tip 80 can be withdrawn from staging chamber 75 and proximally of access port 64 for placement of additional bone growth material into loading chamber 73. The side-loading access port 64 allows placement of the bone growth material without removal of driver 40 or staging tip 80 from housing 60. The additional bone growth material can then be re-packed into staging chamber 75 and dispensing chamber 79 with staging tip 80 by manipulating driver 40.

The threaded engagement of driver 40 with mounting member 22 provides a mechanical advantage in moving the bone growth material through the chambers of housing 60. This mechanical advantage can be useful when the particle size, viscosity or other properties of the bone growth material make displacement through elongated and relatively narrow chambers difficult. Other embodiments contemplate other configurations for translating driver 40 with a mechanical advantage, including ratcheting mechanisms, levers, gears and other mechanisms, for example.

Figure 15:
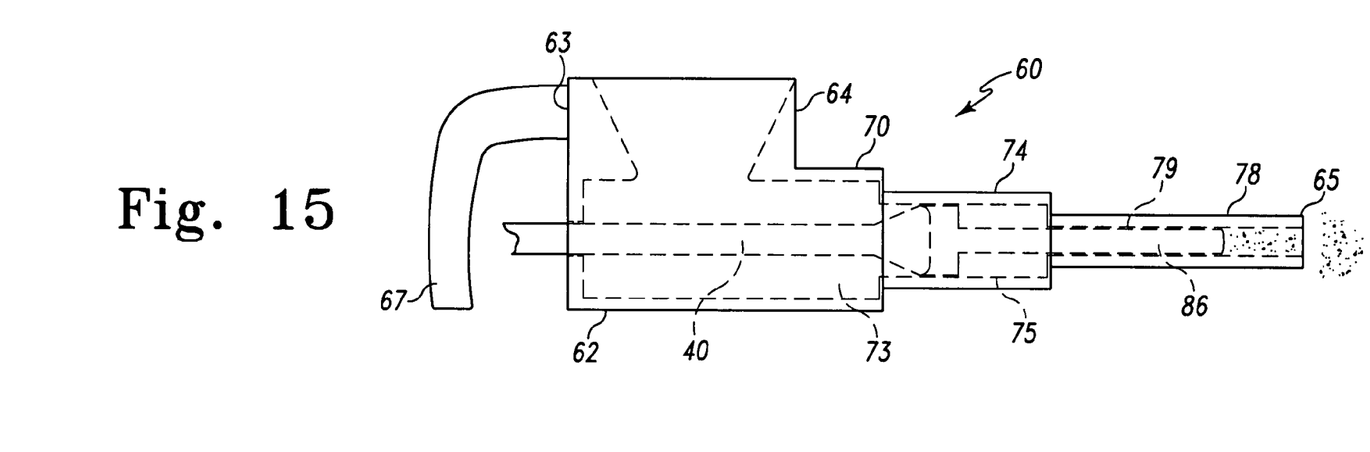
FIG. 15 is an elevation view of the housing and a portion of the driver of the tool of FIG. 1 with bone growth material being dispensed through the dispensing chamber of the housing with the dispensing tip coupled to the driver.

When the desired quantity or maximum quantity of bone growth material has been staged with staging tip 80, a dispensing tip 86 is provided to dispense bone growth material from dispensing chamber 79. Driver 40 is rotated to withdraw staging tip 80 through the proximal end of housing 60. Housing 60 is then quickly and easily removed from mounting member 22 to provide access to gripping mechanism 50 of driver 40. Staging tip 80 can then be removed, and dispensing tip 86 inserted between the gripping members 52 of gripping mechanism 50. Dispensing tip 86 is retracted proximally into mounting member 22 sufficiently to allow placement of arms 66, 67 in interlocking engagement with fingers 30, 31. Dispensing tip 86 can then be distally and axially advanced with driver 40 through the passage 68 to dispensing chamber 79.

Dispensing tip 86 includes a proximal gripping portion 90 sized to be engaged with gripping mechanism 50 and a distal portion 88. Distal portion 88 is received through housing 60 and into dispensing chamber 79. As distal portion 88 is moved through dispensing chamber 79, bone growth material is dispensed or expelled from dispensing portion 78. The insertion of dispensing tip 86 can be limited by contact of gripping portion 90 with the transition between staging chamber 75 and dispensing chamber 79. In one embodiment, dispensing portion 78 of housing 60 includes a first length along axis 61, and distal portion 88 includes a second length along axis 61.

The second length can be greater than the first length so that distal portion 88 projects slightly beyond distal end 65 of dispensing portion 78, facilitating evacuation of bone growth material from dispensing chamber 79.

Staging tip 80 includes a cross-section that conforms to the cross-section of at least one of loading chamber 73 or staging chamber 75. In one form, staging tip 80 conforms to loading chamber 73 and is not positionable in staging chamber 75. The distal end of staging tip 80 abuts the transition between chambers 73, 75 when fully inserted. In another form, staging tip 80 is received in staging chamber 75 and is movable until its distal end is placed into abutting engagement with the transition between staging chamber 75 and dispensing chamber 79. In either embodiment, visualization of the placement and displacement of bone growth material can be facilitated by windows or by the material of housing 60.

Dispensing tip 86 includes distal portion 88 that is sized and shaped to conform to the cross-section of dispensing chamber 79. Gripping portion 90 can abut the transition between chambers 75, 79 to limit the insertion of dispensing tip 86 into housing 60. In the illustrated embodiments, the tips 80, 86 and chambers 75, 79 have a circular cross-section, and dispensing chamber 79 includes a first diameter that is less than a second diameter defined by staging chamber 75. Staging chamber 75 may have a diameter that is less than or the same as the diameter of loading chamber 73. Other embodiments contemplate other shapes for the chambers and tips, including non-circular shapes.

Bone growth material may be dispensed through a distal end opening, one or more side openings, or any combination thereof. It is further contemplated that an extension could be provided that is releasably coupled to dispensing portion 78 to facilitate placement of the bone growth material in locations not otherwise accessible with tool 20. The extension can be angled or flexible relative to dispensing portion 78 to facilitate in placement of the bone growth material in the desired locations.

Housing can be preloaded with bone growth material and handed off to surgeon. In one procedure, an attendant can place bone growth material and pack the bone growth material in at least the staging chamber. The staging tip can be removed and the dispensing tip attached to the driver. The tool can then be handed to the surgeon for placement of the bone growth material at the operative site. Multiple tools can be employed in the same procedure if necessary to accommodate the quantity of bone growth material to be placed. Alternatively, the same delivery tool can be re-packed with bone growth material after delivery of a first quantity of bone growth material.

The delivery tool can be fabricated from a wide variety of materials, including plastics and polymers, metals and metal alloys, glass, or metal, or any combination thereof. The housing can be made from a clear material to allow visualization of the material and internal tool components therein. This allows the positioning and quantity of material and the components to be readily observed by the user.

The delivery tool can be supplied as part of a kit for use in implanting solid, particulate bone growth material. Such material may include, for example, bone graft, allograft chips, autogenous morselized bone graft, strips of autogenous bone graft, demineralized bone matrix in putty, gel, strip, or other forms, xenografts and fired bone. The solids can also be bone graft substitutes, such as hydroxyapatite, calcium carbonate, beta tricalcium phosphate, calcium sulfate or mineralized collagen. Natural or synthetic polymers such as collagen particles, meshes, sponges, and gels, hyaluronic acid and derivatives thereof, liposomes or other natural biomaterials known as potential implants, or carriers of therapeutic agents, such as cytokines, growth factors, cells, antibiotics, analgesics, chemotherapeutic drugs, and the like. As synthetic polymers, there can be alpha-hydroxy polyesters, including polylactic acid, polyglycolic acid and their copolymers, polydioxanone, as well as poly methyl methacrylate, separately, in mixture or in admixture with any of the foregoing therapeutic agents. The delivery tool can be supplied with bone graft substitutes such as hydroxyapatite, calcium carbonate, or calcium sulfate in kit form.

Various modifications to the housing of the delivery tool are contemplated. For example, the size and shape of the housing, access port, and delivery ports may be varied to accommodate different types of materials, differing approaches to the operative site, and differing operative sites.

While the invention has been illustrated and described in detail in the drawings and foregoing description, the same is to be considered as illustrative and not restrictive in character. All changes and modifications that come within the spirit of the invention are desired to be protected.

What is claimed is:

1. A tool for delivery of bone growth material to an operative site, comprising:

a mounting member including an elongated passage extending longitudinally therethrough between a proximal end and an opposite distal end of said mounting member, said mounting member including a distal mounting portion at said distal end and said passage includes a distal end opening at said distal end;

a housing removably mounted to said distal mounting portion of said mounting member, said housing including a sidewall extending about a longitudinal axis, said sidewall defining a loading chamber and a dispensing chamber distal of said loading chamber, said housing further including an access port in said sidewall in communication with said loading chamber, said access port configured to receive bone growth material for depositing in said loading chamber, said housing further including a proximal end wall through which said loading chamber opens, wherein said proximal end wall of said housing is positioned distally of said distal end of said mounting member when said housing is mounted thereto;

bone growth material in said loading chamber; and a driver engaged to said mounting member and said driver extends proximally of said proximal end of said mounting member and into said passage of said mounting member and distally through said distal end opening of said passage and through said proximal end wall of said housing with a distal end portion of said driver received in said loading chamber, said driver being longitudinally movable in said loading chamber to displace bone growth material therein toward a distal end of said dispensing chamber, wherein said distal mounting portion of said mounting member includes a first pair of fingers defining a first U-shaped receptacle on one side of said longitudinal axis and a second pair of fingers defining a second U-shaped receptacle on an opposite side of said longitudinal axis, and said housing includes a flange extending from said proximal end wall, said flange extending between a pair of arms, said pair of arms extending from said flange on opposite sides of said longitudinal axis, each of said arms being slidably positioned in respective ones of said first and second receptacles with said flange in contact with said distal mounting portion of said mounting member.

2. The tool of claim 1, wherein said driver includes a distal gripping assembly and a tip removably engageable to said distal gripping assembly.

3. The tool of claim 2, wherein said tip is selected from a staging tip having a first cross-section with a first diameter at a distal end thereof and a dispensing tip having a second cross-section with a second diameter at a distal end thereof, said second diameter being less than said first diameter.

4. The tool of claim 3, wherein said housing includes a staging chamber between said dispensing chamber and said loading chamber, said staging chamber having a cross-section substantially corresponding to said first diameter and said dispensing chamber having a cross-section substantially corresponding to said second diameter.

5. The tool of claim 4, wherein said dispensing chamber includes a length along said longitudinal axis and said dispensing tip includes a distal end portion extending along said second diameter, said distal end portion having a length that is greater than said length of said dispensing chamber.

6. The tool of claim 1, wherein said driver is threadingly engaged in said passage of said mounting member.

7. A tool for delivery of bone growth material to an operative site, comprising:
a mounting member including an elongated passage extending longitudinally therethrough between a proximal end and an opposite distal end of said mounting member, said mounting member including a distal mounting portion at said distal end and said passage includes a distal end opening at said distal end;
a housing removably mounted to said distal mounting portion of said mounting member, said housing including a sidewall extending about a longitudinal axis, said sidewall defining a loading chamber and a dispensing chamber distal of said loading chamber, said housing including a proximal end wall through which said loading chamber opens, wherein said proximal end wall of said housing is positioned distally of said distal end of said mounting member when said housing is mounted thereto; and
a driver engaged to said mounting member and said driver extends proximally from said proximal end of said mounting member and into said passage of said mounting member and through said distal end opening of said passage to and through said proximal end wall of said housing into said loading chamber, said driver including a distal gripping assembly with a tip removably engaged thereto, wherein said tip is selected from a staging tip having a first cross-section at a distal end thereof and a dispensing tip having a second cross-section at a distal end thereof, said second cross-section being smaller than said first cross-section, each of said staging and dispensing tips being engageable to said driver and longitudinally movable in said loading chamber with said driver to displace bone growth material toward a distal end of said dispensing chamber when engaged to said driver, wherein said distal mounting portion of said mounting member includes a first pair of fingers defining a first U-shaped receptacle on one side of said longitudinal axis and a second pair of fingers defining a second U-shaped receptacle on an opposite side of said longitudinal axis, and said housing includes a flange extending from said proximal end wall, said flange extending between a pair of arms, said pair of arms extending from said flange on opposite sides of said longitudinal axis, each of said arms being slidably positioned in respective ones of said first and second receptacles with said flange in contact with said distal mounting portion of said mounting member.

8. The tool of claim 7, wherein said housing includes a staging chamber between said dispensing chamber and said loading chamber, said staging chamber having a cross-section substantially corresponding in size and shape to said first cross-section and said dispensing chamber having a cross-section substantially corresponding in size and shape to said second cross-section.

9. The tool of claim 8, wherein said dispensing chamber includes a length along said longitudinal axis and said dispensing tip includes a distal end portion extending along said second cross-section, said distal end portion having a length that is greater than said length of said dispensing chamber.

10. The tool of claim 7, wherein said driver is threadingly engaged in said passage of said mounting member.

11. The tool of claim 7, wherein said housing includes an access port in said sidewall in communication with said loading chamber, said access port configured to receive bone growth material for depositing in said loading chamber.

12. The tool of claim 7, wherein said gripping assembly includes a plurality of gripping members spaced radially thereabout, said gripping members being capable of flexing radially outwardly to receive said selected tip therein.

13. A tool for delivery of bone growth material to an operative site, comprising:
a mounting member having a passage extending longitudinally therethrough, said mounting member extending between a proximal end and an opposite distal portion;
a housing removably mounted to and extending distally from said distal portion of said mounting member, said housing including a sidewall extending about a longitudinal axis, said sidewall defining a loading chamber and an elongated dispensing chamber located distally of said loading chamber, said housing further including a proximal end wall through which said loading chamber opens, wherein said proximal end wall of said housing is positioned distally of said distal portion of said mounting member when said housing is mounted thereto, said housing further including an access port in said sidewall in communication with said loading chamber configured to receive bone growth material for depositing in said loading chamber, wherein said housing includes an elongated staging chamber between said dispensing chamber and said loading chamber, said staging chamber having a first cross-sectional size orthogonally to said longitudinal axis and said dispensing chamber having a second cross-sectional size orthogonally to said longitudinal axis that is smaller than said first cross-sectional size;
a driver engaged to said mounting member in said passage of said mounting member and extending through said proximal end wall of said housing with a distal end portion of said driver received in said loading chamber; and
a staging tip and a dispensing tip, each of said staging and dispensing tips being removably engageable to said distal end portion of said driver, wherein said staging tip corresponds in size to said first cross-sectional size of said staging chamber to move bone growth material from said loading chamber through said staging chamber to said dispensing chamber with said driver when said staging tip is engaged thereto and moved longitudinally with said driver through said loading chamber into said staging chamber, and further wherein said dispensing tip corresponds in size to said second cross-sectional size of said dispensing chamber to move bone growth material from said dispensing chamber through an opening of said dispensing chamber when said dispensing tip is engaged to said driver and moved longitudinally with said driver through said dispensing chamber toward said opening, wherein said driver is movable from a first position where said distal end portion of said driver is removed from said loading chamber while said driver is supported in said passage of said mounting member for removing and engaging said staging tip and said dispensing tip with said distal end portion, and said driver is movable longitudinally in said mounting member from said first position through said proximal end wall of said housing into said dispensing chamber with one of said staging tip and said dispensing tip engaged to said distal end portion of said driver, wherein said distal mounting portion of said mounting member includes a first pair of fingers defining a first U-shaped receptacle on one side of said longitudinal axis and a second pair of fingers defining a second U-shaped receptacle on an opposite side of said longitudinal axis, and said housing includes a flange extending from said proximal end wall, said flange extending between a pair of arms, said pair of arms extending from said flange on opposite sides of said longitudinal axis, each of said arms being slidably positioned in respective ones of said first and second receptacles with said flange in contact with said distal mounting portion of said mounting member.

14. The tool of claim 13, wherein said driver includes a distal gripping assembly and said staging tip and said dispensing tip are removably engageable to said distal gripping assembly.

15. The tool of claim 13, wherein said first and second cross-sectional sizes of said staging chamber and said dispensing chamber include a first diameter of said staging chamber and a second diameter of said dispensing chamber, wherein said first diameter is greater than said second diameter, and further wherein said loading chamber includes a cross-sectional size orthogonally to said longitudinal axis that is greater than first cross-sectional size.

16. The tool of claim 13, wherein said dispensing chamber includes a length along said longitudinal axis and said dispensing tip includes a length that is greater than said length of said dispensing chamber.

17. The tool of claim 13, wherein said driver is threadingly engaged in said passage of said mounting member.

\* \* \* \* \*

UNITED STATES PATENT AND TRADEMARK OFFICE
CERTIFICATE OF CORRECTION

PATENT NO. : 7,578,823 B2  Page 1 of 1
APPLICATION NO. : 11/118817
DATED : August 25, 2009
INVENTOR(S) : Eric Steven Heinz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this

Seventh Day of September, 2010

David J. Kappos
*Director of the United States Patent and Trademark Office*